(12) United States Patent
Hayakawa

(10) Patent No.: US 11,077,602 B2
(45) Date of Patent: Aug. 3, 2021

(54) BLOW-MOLDING MACHINE AND METHOD OF STERILIZING THE SAME

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 16/713,160

(22) Filed: Dec. 13, 2019

(65) Prior Publication Data
US 2020/0114566 A1   Apr. 16, 2020

Related U.S. Application Data

(63) Continuation of application No. 15/543,044, filed as application No. PCT/JP2016/057092 on Mar. 8, 2016, now Pat. No. 10,543,636.

(30) Foreign Application Priority Data

Mar. 9, 2015   (JP) ................................. 2015-045645

(51) Int. Cl.
*B29C 49/46*   (2006.01)
*B65B 55/10*   (2006.01)
(Continued)

(52) U.S. Cl.
CPC .............. *B29C 49/46* (2013.01); *A61L 2/208* (2013.01); *A61L 2/22* (2013.01); *B29C 49/12* (2013.01); *B29C 49/42* (2013.01); *B29C 49/4289* (2013.01); *B29C 49/64* (2013.01); *B65B 55/10* (2013.01); *B29C 49/06* (2013.01); *B29C 49/28* (2013.01); *B29C 2049/1285* (2013.01); *B29C 2049/4679* (2013.01); *B29C 2049/4694* (2013.01); *B29C 2049/4892* (2013.01); *B29K 2105/258* (2013.01); *B29L 2031/7158* (2013.01)

(58) Field of Classification Search
CPC ............ A61L 2/22; A61L 2/208; B29C 49/46
See application file for complete search history.

(56) References Cited

U.S. PATENT DOCUMENTS 6,692,684 B1 * 2/2004 Nantin ................... B65B 55/06
264/521
2003/0165400 A1   9/2003 Hayakawa et al.
(Continued)

FOREIGN PATENT DOCUMENTS

EP   2 283 991 A2   2/2011
EP   2 394 950 A1   12/2011
(Continued)

OTHER PUBLICATIONS

International Search Report and Written Opinion (Application No. PCT/JP2016/057092) dated Apr. 26, 2016.
(Continued)

*Primary Examiner* — Sean E Conley
(74) *Attorney, Agent, or Firm* — Burr & Brown, PLLC

(57) ABSTRACT

To simply sterilize a blow-molding machine. A mist or gas of hydrogen peroxide or a mixture thereof is introduced through a valve block disposed adjacent to a molding die, thereby sterilizing at least the molding die and an extension rod that extends into the molding die through the valve block.

3 Claims, 5 Drawing Sheets

(51) Int. Cl.
*B29C 49/42* (2006.01)
*B29C 49/12* (2006.01)
*A61L 2/20* (2006.01)
*A61L 2/22* (2006.01)
*B29C 49/64* (2006.01)
*B29C 49/06* (2006.01)
*B29C 49/48* (2006.01)
*B29C 49/28* (2006.01)
*B29K 105/00* (2006.01)
*B29L 31/00* (2006.01)

(56) References Cited

U.S. PATENT DOCUMENTS

| | | |
|---|---|---|
| 2006/0110483 A1 | 5/2006 | Damerow et al. |
| 2010/0303946 A1 | 12/2010 | Voth |
| 2011/0037187 A1 | 2/2011 | Winzinger et al. |
| 2011/0037188 A1 | 2/2011 | Hirdina |
| 2011/0146202 A1 | 6/2011 | Imatani et al. |
| 2011/0265894 A1 | 11/2011 | Yamamoto |
| 2012/0164258 A1 | 6/2012 | Dordoni |
| 2012/0286456 A1 | 11/2012 | Handschuh et al. |
| 2012/0286459 A1 | 11/2012 | Neubauer et al. |
| 2014/0017132 A1 | 1/2014 | Nakata et al. |
| 2015/0001747 A1 | 1/2015 | Winzinger |

FOREIGN PATENT DOCUMENTS

| | | |
|---|---|---|
| EP | 2 522 485 A1 | 11/2012 |
| EP | 2821204 A1 | 7/2013 |
| EP | 3109030 A1 | 2/2015 |
| JP | 2000-326935 A1 | 11/2000 |
| JP | 2005-520707 A1 | 7/2005 |
| JP | 2009-161253 A1 | 7/2009 |
| JP | 2010-274651 A1 | 12/2010 |
| JP | 2011-042169 A1 | 3/2011 |
| JP | 2011-051337 A1 | 3/2011 |
| JP | 2011-232015 A1 | 11/2011 |
| JP | 2012-236414 A1 | 12/2012 |
| JP | 2013-504456 A1 | 2/2013 |
| JP | 2014-195713 A1 | 10/2014 |
| JP | 2014-240305 A1 | 12/2014 |
| WO | 2013/099789 A1 | 7/2013 |

OTHER PUBLICATIONS

Extended European Search Report (Application No. 16761740.6) dated Aug. 30, 2018.

* cited by examiner

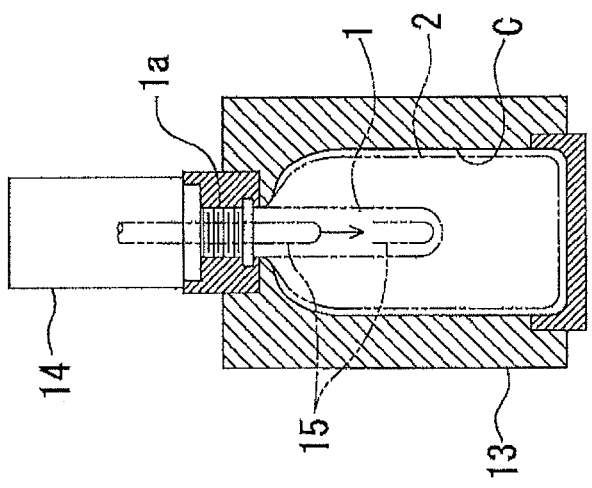
FIG.2(C) MOLDING
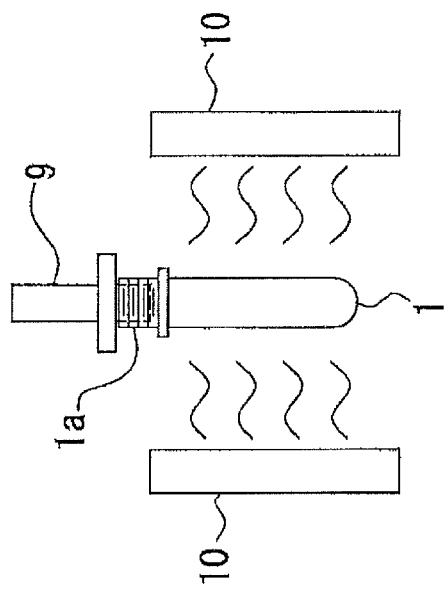
FIG.2(B) HEATING
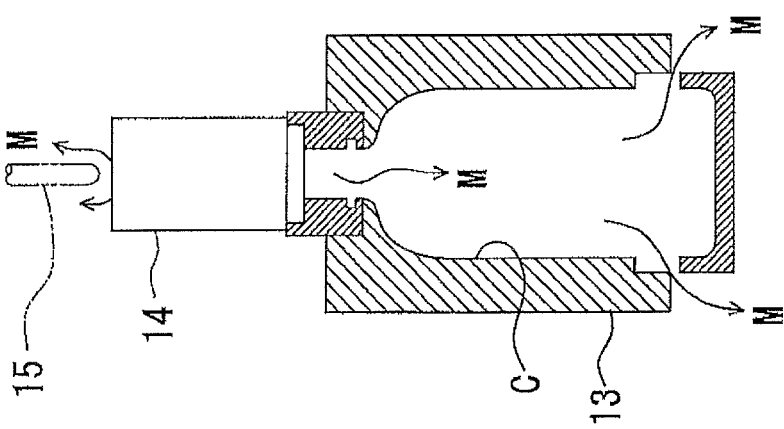
FIG.2(A) STERILIZATION OF INTERIOR AND EXTERIOR OF MOLDING DIE AND THE LIKE

BLOW-MOLDING MACHINE AND METHOD OF STERILIZING THE SAME

CROSS REFERENCE TO RELATED APPLICATIONS

This application is a continuation of U.S. application Ser. No. 15/543,044, filed Jul. 12, 2017, which in turn is the National Stage entry of International Application No. PCT/JP2016/057092, filed Mar. 8, 2016, which designated the United States, the entireties of which are incorporated herein by reference.

FIELD OF THE INVENTION

The present invention relates to a blow-molding machine and a method of sterilizing the same.

BACKGROUND OF THE INVENTION

It has been proposed to sterilize a preform before the preform is molded into a container, such as a bottle, in a molding die in a blow-molding machine (see Patent Document 1, for example). The bottle can be filled with an aseptic content and sealed to produce an aseptic package.

In operation of the blow-molding machine, various malfunctions can occur in the blow-molding machine. If a malfunction occurs, the blow-molding machine needs to be stopped to open a cover of a chamber or the like surrounding the blow-molding machine and open the molding die or the like for internal inspection. If the blow-molding machine is opened, disassembled and maintained, bacteria from the operator or environment can enter the blow-molding machine and adhere to the molding die, an extension rod and the like and further to the preform or bottle, and thus the aseptic package cannot be produced.

To avoid this, a cleaning in place (CIP) system is provided as means for sterilizing the interior of the blow-molding machine after the blow-molding machine is opened. The CIP system can clean a valve block for controlling blow air or the like, for example, without the need of disassembling the blow-molding machine (see Patent Document 2, for example).

Furthermore, it has been proposed to clean the interior of a blow-molding die by opening the die and blasting a cleaner to the inner wall surface of the die from a cleaning nozzle or by opening the die and blasting a cleaner into the die from the extension rod (see Patent Documents 3 and 4, for example).

PRIOR ART DOCUMENT

Patent Document

Patent Document 1: Japanese Patent Laid-Open Publication No. 2000-326935
Patent Document 2: Japanese Patent Laid-Open Publication No. 2010-274651
Patent Document 3: Japanese Patent Laid-Open Publication No. 2011-42169
Patent Document 4: Japanese Patent Laid-Open Publication No. 2011-51337

SUMMARY OF THE INVENTION

Problems to be Solved by the Invention

The conventional CIP system and the method of injecting a cleaner into a die from an extension rod have a problem that a large-scale device is needed to circulate the cleaner. The method of injecting a cleaner into a die from an extension rod and the method of opening a die and injecting a cleaner to the inner wall surface of the die from a cleaning nozzle require drying of the interior of the blow-molding machine after cleaning, which requires much time and energy and leads to a substantial decrease of the availability of the blow-molding machine.

An object of the present invention is to solve the problems described above.

Means for Solving the Problems

To attain the object described above, the present invention adopts the configurations described below.

Note that reference numerals in parentheses are given to facilitate understanding of the present invention and are not intended to limit the scope of the present invention.

Specifically, a method of sterilizing a blow-molding machine according to the present invention is characterized in that a mist or gas of hydrogen peroxide or a mixture thereof is introduced through a valve block (14) disposed adjacent to a molding die (13) to sterilize at least the molding die (13) and an extension rod (15) that extends into the molding die (13) through the valve block (14).

In the method of sterilizing a blow-molding machine according to the present invention, the extension rod (15) may be covered by a housing box (26) when the extension rod (15) is removed from the molding die (13).

In the method of sterilizing a blow-molding machine according to the present invention, a volatile substance may be added to the mist or gas of hydrogen peroxide or the mixture thereof.

A blow-molding machine according to the present invention comprises a transfer device that transfers a preform (1) and a container (2) from where the preform (1) is supplied to the blow-molding machine to where the preform (1) is molded into the container (2), a heating part (3) that heats the preform (1) to a blow molding temperature, a molding die (13) that molds the preform (1) into the container (2) by blow air, the heating part (3) and the molding die (13) being sequentially arranged from an upstream side to a downstream side along the transfer device, a valve block (14) disposed adjacent to the molding die (13), and an extension rod (15) capable of protruding into and retracting from an interior of the molding die (13) through the valve block (14), and is characterized in that in sterilization of the blow-molding machine, the molding die (13) is opened, the extension rod (15) is retracted from the interior of the molding die (13), and then a mist or gas of hydrogen peroxide or a mixture thereof is supplied to the molding die (13) and the extension rod (15) through the valve block (14).

The blow-molding machine according to the present invention may further comprise a housing box (26) that covers the extension rod (15) when the extension rod (15) is removed from the molding die (13) through the valve block (14).

In the blow-molding machine according to the present invention, a volatile substance may be added to the mist or gas of hydrogen peroxide or the mixture thereof.

Effects of the Invention

According to the method of sterilizing a blow-molding machine according to the present invention, the interior and exterior of the molding die (13) and the extension rod (15) are sterilized by opening the molding die (13), retracting the extension rod (15) out of the molding die (13) through the valve block (14) adjacent to the molding die (13), and introducing a mist or gas of hydrogen peroxide or a mixture thereof to the interior and exterior of the molding die (13) and the extension rod (15) through the valve block (14). Thus, unlike the conventional CIP system and the method of injecting a cleaner into the molding die from the extension rod, the method according to the present invention does not require a large-scale device to circulate the cleaner. The blow-molding machine can be quickly sterilized with a simpler device. In addition, unlike the conventional method of injecting a cleaner into the molding die from the extension rod and the conventional method of opening the molding die and injecting a cleaner to the inner wall surface of the molding die from a cleaning nozzle, the method according to the present invention does not require drying of the cleaner after sterilization, so that the time and energy required for sterilization of the blow-molding machine can be reduced, and the availability of the blow-molding machine can be increased.

In addition, according to the present invention, if the extension rod (15) is covered by the housing box (26) when the extension rod (15) is removed from the molding die (13), the extension rod (15) can be more properly sterilized.

In addition, according to the present invention, if a volatile substance is added to the mist or gas of hydrogen peroxide or the mixture thereof, the mist or gas of hydrogen peroxide or the mixture thereof can be efficiently vaporized, and any heating process for vaporizing the hydrogen peroxide can be omitted. Thus, corrosion of the blow-molding machine due to the heating process can be avoided.

BRIEF DESCRIPTION OF THE DRAWINGS

FIGS. 2(A)-2(C) are diagrams for illustrating steps of a method of sterilizing the blow-molding machine.

DETAILED DESCRIPTION OF THE INVENTION

In the following, an embodiment of the present invention will be described.

Figure 1:
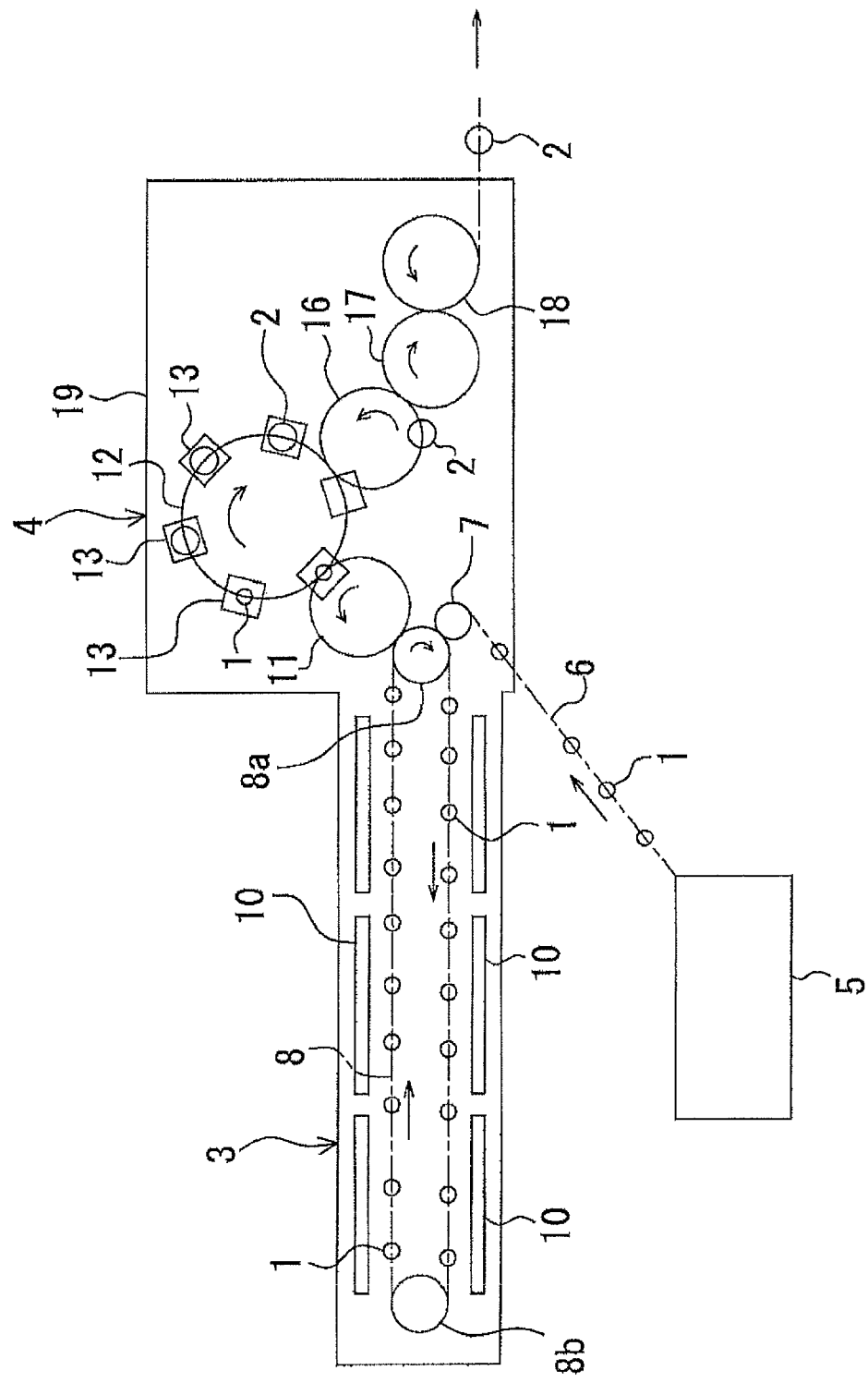
FIG. 1 is a schematic plane view of a blow-molding machine according to the present invention.

As shown in FIG. 1, a blow-molding machine includes a transfer device that transfers a preform 1 (see FIG. 2(B)) and a bottle 2 (see FIG. 2(C)) from where the preform 1 is supplied to where the preform 1 is molded into the bottle 2.

In the blow-molding machine, a heating part 3 that heats the preform 1 to a blow-molding temperature, and a molding part that molds the preform 1 into the bottle 2 by blow air are arranged in this order from the upstream side to the downstream side along the transfer device.

The heating part 3 and the molding part 4 are covered by a chamber 19, which serves as a protective cover. The chamber 19 is constantly supplied with aseptic air from an aseptic air supply source (not shown) to keep a positive pressure.

On the upstream side of the transfer device, there is provided a preform supplying machine 5 that successively supplies preforms 1 at predetermined intervals.

As shown in FIG. 2(B), the preform 1 is a bottomed tubular body similar to a test tube and is formed from polyethylene terephthalate (PET), for example, by injection molding or the like. The preform 1 is eventually to be shaped by blow molding into the bottle 2, which is a container, as shown in FIG. 2(C). However, a mouth portion 1a, a male thread and the like similar to those of the finished bottle 2 are formed on the preform 1 in the early stage of the molding of the preform 1. The preform 1 is sterilized in advance of being fed from the preform supplying machine 5 to the heating part 3 of the blow-molding machine. Alternatively, the preform 1 may be sterilized by blasting a mist or gas of hydrogen peroxide or a mixture thereof, which is a sterilizer produced by a vaporizer 32 described later or a similar vaporizer, while the preform 1 is being fed from the preform supplying machine 5 to the heating part 3 of the blow-molding machine.

An endless conveyor 6, which is a delivery device for the preform 1, extends from the preform supplying machine 5 to the blow-molding machine.

The heating part 3 is disposed in a part of the blow-molding machine where the blow-molding machine receives the preform 1 from the preform supplying machine 5.

The endless conveyor 6 extends into the heating part 3 and is provided with a wheel 7 at its end in the heating part 3. The endless conveyor 6 and the wheel 7 are provided with a gripper or the like (not shown) that holds the preform 1 during conveyance.

The heating part 3 has a furnace chamber that is elongated in one direction. In the furnace chamber, an endless chain 8 serving as a transfer device for the preform extends between a pair of pulleys 8a and 8b that are disposed to be opposed to each other in a horizontal plane. The endless conveyor 6 described above is connected to the pulley 8a disposed on the side of an inlet port of the furnace chamber.

A large number of holding members 9 for preforms 1 like that shown in FIG. 2(B) are attached to the endless chain 8 at regular intervals. Each holding member 9 can rotate on its axis while moving with the endless chain 8. The holding member 9 is formed as a spindle and has a plurality of ball-shaped elastic bodies (not shown) embedded in an outer surface of a lower part thereof. Once the holding member 9 is inserted into the mouth portion 1a of the preform 1, the elastic bodies are elastically deformed to hold the preform 1 on the holding member 9 as shown in FIG. 2(B).

If the holding member 9 is formed as a mandrel rather than the spindle, the preform 1 can be supported in an inverted position during conveyance.

A heater 10 that emits infrared rays is attached to an inner wall surface of the furnace chamber of the heating part 3 along a forward and a return run of the endless chain 8.

After the preform 1 is received by the holding member 9 via the endless conveyor/chute 6 and the wheel 7, the preform 1 travels along the inner wall surface of the heating part 3 while rotating on its axis. The preform 1 conveyed on the holding member 9 is heated by the heater 10 provided over the inner wall surface of the heating part 3, as shown in FIG. 2(B). When the preform 1 is travelling in the heating part 3, the preform 1 rotates on its axis as the holding member 9 rotates, and is uniformly heated by the heater 10 until the preform 1 excluding the mouth portion 1a is heated to 90° C. to 130° C., which is a temperature range suitable for blow molding. The temperature of the mouth portion 1a is kept to be equal to or lower than 70° C., at which no deformation or the like occurs, so that sealing between the mouth portion 1a and a cap (not shown) to be fitted on the mouth portion 1a is not compromised.

At a connection of the pulley 8a at one end of the endless chain 8 to the return run of the endless chain 8, there is provided a row of wheels 11 and 12 that receive the preform 1 heated by the heater 10 and feed the preform 1 into the molding part 4.

The upstream wheel 11 is provided with a gripper (not shown) on the circumference thereof, and the gripper grasps the preform 1 at the mouth portion 1a thereof during conveyance of the preform 1 to the following downstream wheel 12.

The downstream wheel 12 is provided with a plurality of molding dies 13 at predetermined intervals. The molding die 13 is a split die that receives the heated preform 1 from the gripper of the upstream wheel 11 and molds the preform 1 into the bottle 2 by blow air. The molding dies 13 rotate at a constant velocity around the wheel 12 as the wheel 12 rotates.

Figure 3:
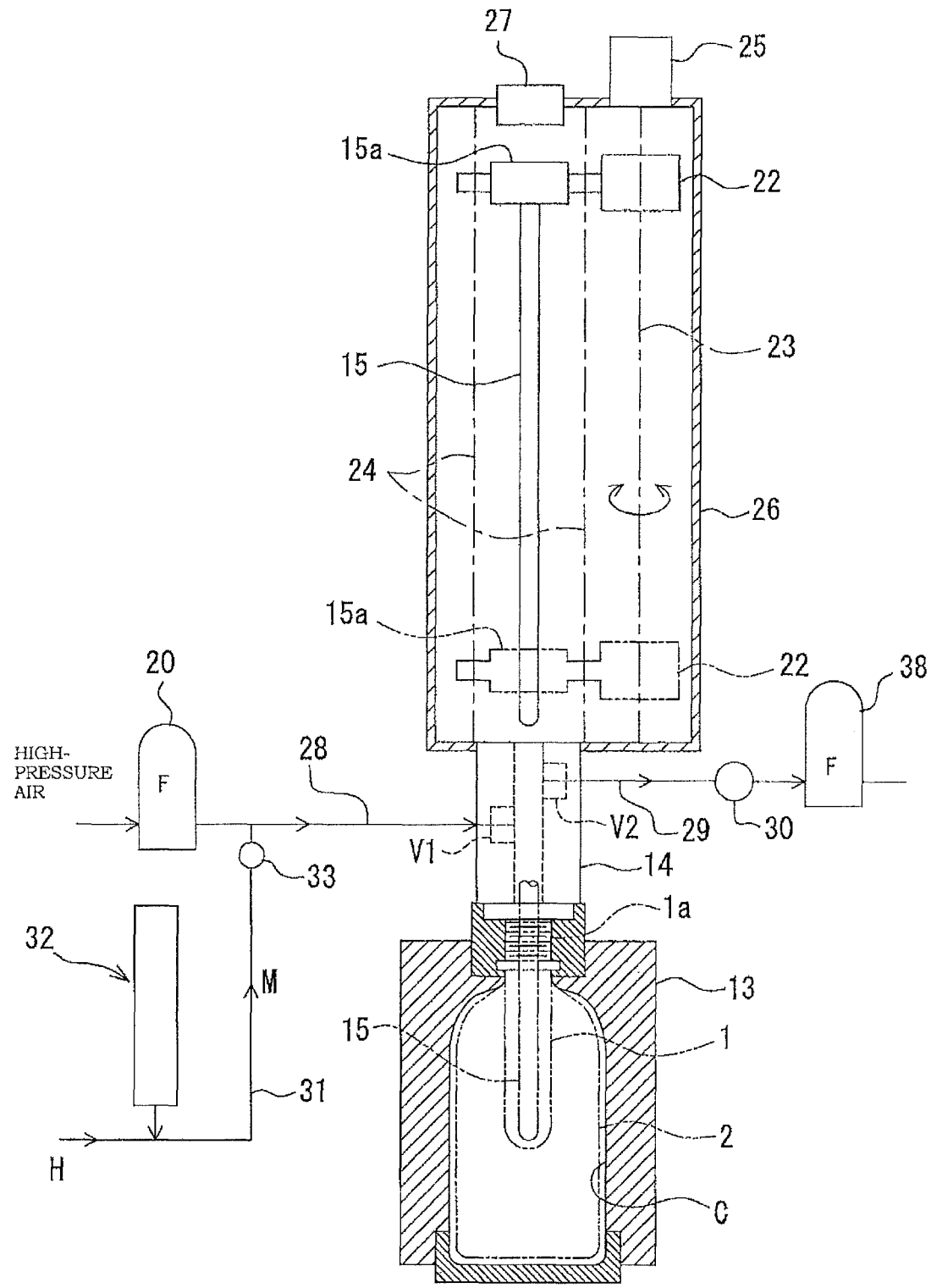
FIG. 3 is a schematic vertical cross-sectional view of a molding die and its surroundings.

As shown in FIGS. 2(C) and 3, a valve block 14 is disposed adjacent to each molding die 13. The valve block 14 is mainly intended to control supply, discharge or the like of the blow air, and a vertical through-hole is formed along the center line thereof.

Piping 28 for supplying blow air through a predetermined valve V1 therein and piping 29 for discharging used blow air through another valve V2 are connected to the valve block 14.

An upstream part of the piping 28 extends to a high-pressure air source (not shown), such as a compressor. The part of the piping 28 extending from the high-pressure air source is provided with an aseptic filter 20 that filters out bacteria or the like.

The discharge piping 29 is provided with a silencer 30 and an aseptic filter 38, which are arranged in this order from the upstream side to the downstream side. As required, a catalyst that decomposes hydrogen peroxide is provided downstream of the aseptic filter 38.

A conduit 31 for supplying a mist or gas of hydrogen peroxide or a mixture thereof to the molding die 13 or the like is connected to the part of the piping 28 extending from the high-pressure air source at a point downstream of the aseptic filter 20. A vaporizer 32 for generating a mist or gas of hydrogen peroxide or a mixture thereof is attached to the conduit 31. The conduit 31 is provided with a blow air source (not shown) that feeds aseptic hot air toward the vaporizer 32 at a point upstream of the vaporizer 32, and is provided with a valve 33 that opens and closes the conduit 31 at a point downstream of the vaporizer 32. In advance of molding of the bottle 2, the valve 33 is opened to sterilize the molding die 13 or the like.

Figure 4:
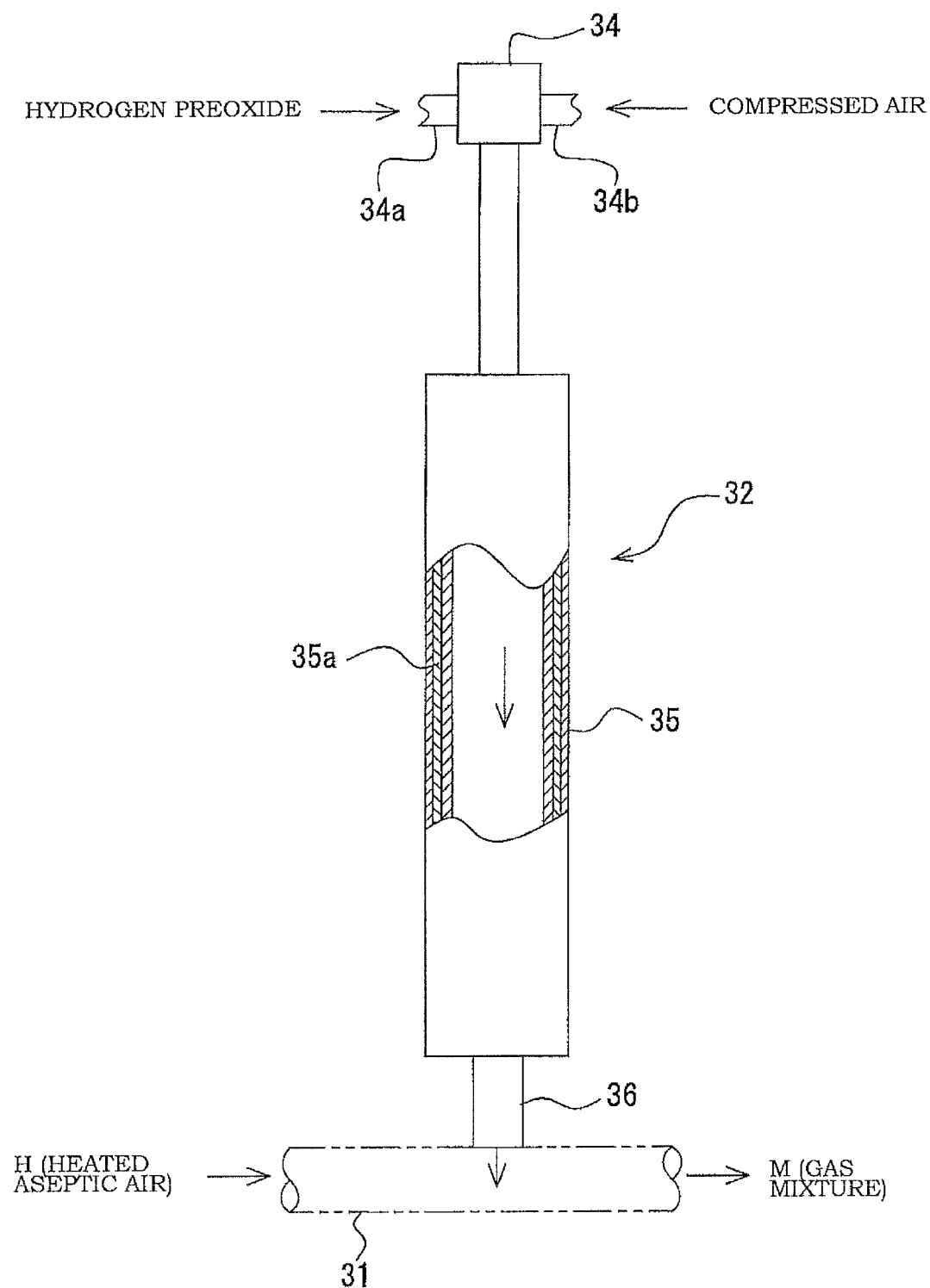
FIG. 4 is a vertical cross-sectional view of an example of a vaporizer that generates a mist or gas of hydrogen peroxide or a mixture thereof.

As the vaporizer 32, one which has the structure shown in FIG. 4 is used, for example.

The vaporizer 32 includes a hydrogen peroxide supplying portion 34 that is a twin-fluid spray that supplies a hydrogen peroxide solution serving as a sterilizer in the form of drops and an vaporizing portion 35 that evaporates a spray of hydrogen peroxide supplied from the hydrogen peroxide supplying portion 34 by heating the spray of hydrogen peroxide to a temperature equal to or higher than the boiling point thereof and equal to or lower than the non-degradable temperature thereof. The hydrogen peroxide supplying portion 34 is configured to receive the hydrogen peroxide solution and compressed air from a hydrogen peroxide supply path 34a and a compressed air supply path 34b, respectively, and sprays the hydrogen peroxide solution into the vaporizing portion 35. The vaporizing portion 35 is a pipe that incorporates a heater 35a disposed between inner and outer walls thereof, and heats and vaporizes the spray of hydrogen peroxide blasted into the pipe. The vaporized hydrogen peroxide is ejected in the form of mist or gas or a mixture thereof from a nozzle 36 to the outside of the vaporizer 32.

The nozzle 36 is coupled to the conduit 31 in a crossing manner. Thus, the mist or the like ejected from the nozzle 36 is mixed with aseptic hot air H flowing in the conduit 31 to form a gas mixture M, and the gas mixture M flows to the valve block 14 through the conduit 31 and the piping 28. The gas mixture M may also be produced by increasing the flow rate of the compressed air supplied to the vaporizer 32 from the compressed air supply path 34b. In that case, the supply of the hot air H shown in FIG. 4 can be omitted.

In addition, an extension rod 15 that can protrude into and retract from the molding die 13 through the through-hole of the valve block 14 is provided. The extension rod 15 is disposed in such a manner that the central axis thereof is aligned with the extension of the central axis of the molding die 13 and the preform 1 held in the molding die 13.

A driving part that makes the extension rod 15 perform the protrusion and retraction operations described above is provided for the extension rod 15. More specifically, a nut 22 is coupled to a rear end of the extension rod 15, and a feeding threaded bar 23 that extends in parallel with the extension rod 15 is screwed into the nut 22. In order to precisely achieve the protrusion and retraction operations of the extension rod 15 described above, a guide member 24 that extends in parallel with the feeding threaded bar 23 is provided. One or more rail-shaped or bar-shaped guide members 24 are provided, and the guide members 24 are slidably engaged with a base portion 15a of the extension rod 15 at the rear end thereof or with the nut 22.

The feeding threaded bar 23 is coupled to an output shaft of a servomotor 25 at one end thereof and thus can be rotated in both forward and reverse directions.

The extension rod 15, the feeding threaded bar 23 that is the driving part therefor and the like are covered by and sealed in a housing box 26. The housing box 26 may be divided by a partition wall (not shown) into a section that houses the extension rod 15 and a section that houses the feeding threaded bar 23.

Reference numeral 27 denotes a ventilation part through which the gas mixture M filling the housing box 26 passes to the outside of the housing box 26 as described later.

The ventilation part 27 is a simple ventilation hole, and the gas mixture M filling the housing box 26 is guided into the chamber 19 outside the housing box 26 through the ventilation part 27 along with the sterilizer contained therein. Thus, the interior of the chamber 19 is also sterilized by the sterilizer.

In the ventilation part 27, as required, a filter that catches and decomposes the sterilizer contained in the gas mixture and allows only air to flow out of the housing box 26 is provided.

The molding die 13 rotates with the wheel 12 and is opened at a position where the molding die 13 is adjacent to a conveyance wheel 16. When the bottle 2 is molded in the molding die 13, the molded bottle 2 is passed from the opened molding die 13 to a gripper (not shown) of the conveyance wheel 16.

As shown in FIG. 1, another row of wheels 17 and 18 is connected to the conveyance wheel 16. The molded bottle is passed from the wheel 16 to the wheel 17 and then from the wheel 17 to the wheel 18 and then conveyed to the outside of the blow-molding machine.

A volatile substance is preferably added to the mist or gas of hydrogen peroxide or a mixture thereof described above. The volatile substance is preferably ethanol, propanol or isopropanol, for example. If the volatile substance is added to the mist or gas of hydrogen peroxide or a mixture thereof, the mist or gas of hydrogen peroxide or a mixture thereof can be efficiently vaporized in the molding die 13, and the heating process for vaporizing the hydrogen peroxide can be omitted, so that corrosion of the molding die 13 due to the heating process can be avoided. In addition, since the hydrogen peroxide concentration can be reduced by adding the volatile substance, the hydrogen peroxide can be prevented from remaining in the blow-molding machine after sterilization. Such a sterilizer preferably contains the added volatile substance such as ethanol as a main component and preferably contains 0.1% by weight to 35% by weight of hydrogen peroxide. In order to further reduce corrosivity and achieve a desired sterilization effect (6 Log for *B. atrophaesu* spores), the concentration of hydrogen peroxide is more preferably 1 to 5% by weight.

Next, an operation of the blow-molding machine described above will be described.

(1) To perform a bottle molding operation, the preform 1 is conveyed into the heating part 3 of the blow-molding machine by the endless conveyor/chute 6 of the preform supplying machine 5.

As the preform 1, one which is sterilized in advance may be used.

(2) Once the preform 1 is introduced into the heating part 3, the preform 1 is held by the holding member 9 attached to the endless chain 8 and is heated by the heater 10 to a temperature suitable for molding while traveling as the endless chain 8 moves (see FIG. 2(B)).

If the preform 1 is not sterilized in advance, the preform 1 can be sterilized by blasting a mist or gas of hydrogen peroxide or a mixture thereof to the preform 1 before the preform 1 reaches the heating part 3, when the preform 1 enters the heating part 3, or before preform 1 having exited the heating part 3 reaches the molding die 13, for example. In this process, if a volatile substance is added to the hydrogen peroxide, the hydrogen peroxide can be efficiently vaporized, and the hydrogen peroxide can be prevented from remaining in the preform after the sterilization.

(3) The preform 1 heated to the predetermined temperature is passed from the holding member 9 on the endless chain 8 to the gripper on the wheel 11 and then is received in the molding die 13, which rotates with the wheel.

(4) Once the molding die 13 receives the preform 1 and is closed, the servomotor 25 rotates in the forward direction, thereby lowering the extension rod 15 from the interior of the valve block 14 into the preform 1 toward the bottom thereof to expand the preform 1. When the extension rod 15 completely protrudes, a valve part (not shown) provided on the extension rod 15 at a midpoint thereof closes the opening of the valve block 14.

Blow air is then blasted into the preform 1 from the piping 28 for supplying blow air through the predetermined valve V1 in the valve block 14 to expand the preform 1 into the bottle 2, which is a container, in a cavity C of the molding die 13 (see FIG. 2(C)).

(5) Once the bottle 2 is molded, the valve block 14 is operated to discharge the used blow air to the outside of the molding die 13 through the valve V2 and the piping 29. In this process, the silencer 30 reduces the discharge noise.

In addition, once the molding of the bottle 2 is completed, the servomotor 25 rotates in the reverse direction, thereby retracting the extension rod 15 to the outside of the molding die 13.

(6) When the preform 1 is molded into the bottle 2, and the molding die 13 reaches a position where the molding die 13 is adjacent to the conveyance wheel 16, the molding die 13 is opened, and the molded bottle 2 is released.

(7) The released bottle 2 is received by the gripper (not shown) on the conveyance wheel 16 and conveyed to the outside of the blow-molding machine.

(8) As described above, when the bottle 2 is being manufactured in the blow-molding machine, some malfunction can occur in the blow-molding machine. In that event, the operator stops the blow-molding machine, opens the chamber 19 surrounding the blow-molding machine, and opens the molding die 13 or the like for internal inspection or cleaning.

If the blow-molding machine is opened, bacteria from a human or environment enter the blow-molding machine and adhere to the molding die 13, the extension rod 15 and the like and further to the preform 1 or bottle 2, and thus the aseptic package cannot be produced. Thus, before the blow-molding machine is brought into operation again, the interior of the blow-molding machine needs to be sterilized.

(9) Thus, after the inspection or the like of the interior of the blow-molding machine, and the chamber 19 is closed, the operations described below are performed.

At this stage, the molding die 13 has been opened, and the extension rod 15 has been retracted from inside the molding die 13 into the housing box 26 as a result of the servomotor 25 having rotated in the reverse direction.

The valve 33 on the conduit 31 is opened, and the gas mixture M containing hydrogen peroxide flows into the molding die 13 through the conduit 31 and the piping 28. Since the molding die 13 is open, the gas mixture M further flows to the outside of the molding die 13. In this way, the interior and exterior of the molding die 13 is sterilized (see FIG. 2(A)).

In addition, since the extension rod 15 has been retracted, and the valve part at a midpoint of the extension rod 15 is spaced apart from the opening of the valve block 14, the opening of the valve block 14 is open. Thus, the gas mixture M containing hydrogen peroxide also flows into the housing box 26 and sterilizes the whole of the extension rod 15 in the housing box 26, the feeding threaded bar 23 of the driving part, the inner surface of the housing box 26 and the like.

The gas mixture M having flown into the housing box 26 flows out of the housing box 26 into the chamber 19 through the ventilation part 27. Thus, the hydrogen peroxide contained in the gas mixture M having passed through the ventilation part 27 sterilizes the molding part 4 in the chamber 19.

(10) After the interior of the chamber 19 is sterilized by the hydrogen peroxide contained in the gas mixture M, aseptic air is supplied into the chamber 19 from an aseptic air supplying apparatus (not shown) to keep the aseptic state of the interior of the chamber 19.

As required, the aseptic air supplying apparatus may be provided with a heater, and heated aseptic air may be blasted into the chamber 19.

(11) After the sterilization of the interior of the blow-molding machine is completed as described above, the valve 33 is closed to stop supply of the gas mixture M to the valve block 14 and the molding die 13.

The bottles 2 are produced by repeating the operations (1) to (7) described above.

Figure 5:
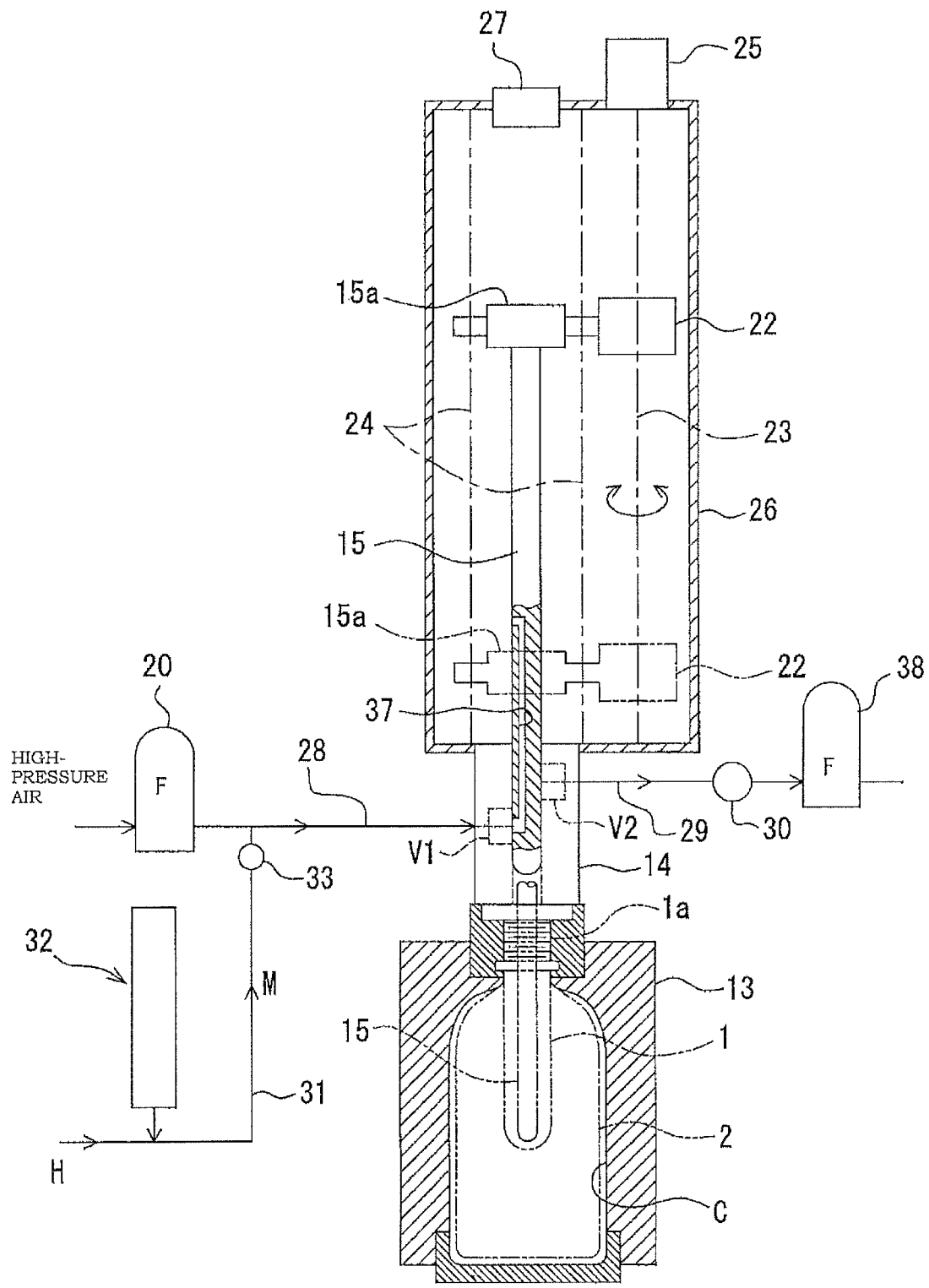
FIG. 5 is a schematic vertical cross-sectional view of the molding die and its surroundings in the case where an extension rod according to another aspect is used.

In the step (9), as shown in FIG. 5, a tunnel-like channel 37 for passing the gas mixture M may be formed in a middle part of the extension rod 15, and the servomotor 25 may be controlled so that the extension rod 15 partially remains in the valve block 14. In that case, the gas mixture M flows into the housing box 26 through the valve V1 and the tunnel-like channel 37.

Sterilization of the chamber 19 and the molding die 13 can also be performed without using the gas mixture M shown in FIG. 3. That is, another vaporizer like the vaporizer 32 shown in FIG. 4 can be attached to the chamber 19 to spray a gas or mist containing hydrogen peroxide into the chamber 19, thereby sterilizing the blow-molding machine in the chamber 19.

REFERENCE NUMERALS 1 preform
2 container (bottle)
13 molding die
14 valve block
15 extension rod
26 housing box

The invention claimed is:

1. A blow-molding machine, comprising:
a transfer device that transfers a preform and a container from where the preform is supplied to the blow-molding machine to where the preform is molded into the container,
a heating part that heats the preform to a blow molding temperature,
a molding part, which comprises a molding die, that molds the preform into the container by blow air, the heating part and the molding part being sequentially arranged from an upstream side to a downstream side along the transfer device,
a chamber, which has an interior, that covers the heating part and the molding part,
a valve block disposed adjacent to the molding die, and an extension rod capable of protruding into and retracting from an interior of the molding die through the valve block, and
a housing box that covers the extension rod, the housing box having a ventilation part that passes a mist or gas of hydrogen peroxide or a mixture thereof from the housing box to the interior of the chamber to sterilize the molding part in the chamber.

2. A blow-molding machine according to claim 1, further comprising:
an aseptic air supplying apparatus that supplies an aseptic air into the chamber.

3. A blow-molding machine according to claim 2, further comprising:
a heater that heats the aseptic air supplied by the aseptic air supplying apparatus.

* * * * *